(12) United States Patent
Dimatteo et al.

(10) Patent No.: US 11,878,122 B2
(45) Date of Patent: *Jan. 23, 2024

(54) FILTER ASSEMBLY AND AIRWAY PRESSURE SUPPORT SYSTEM EMPLOYING SAME

(71) Applicant: KONINKLIJKE PHILIPS N.V., Eindhoven (NL)

(72) Inventors: Mark William Dimatteo, Irwin, PA (US); Mark Wayne Barclay, Saxonburg, PA (US); Joseph Kromka, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 407 days.

This patent is subject to a terminal disclaimer.

(21) Appl. No.: 17/193,034

(22) Filed: Mar. 5, 2021

(65) Prior Publication Data

US 2022/0054789 A1    Feb. 24, 2022

Related U.S. Application Data

(62) Division of application No. 15/561,795, filed as application No. PCT/EP2016/056766 on Mar. 29, 2016, now Pat. No. 10,967,145.

(Continued)

(30) Foreign Application Priority Data

May 1, 2015 (EP) ..................................... 15166118

(51) Int. Cl.
*A61M 16/10* (2006.01)
*A61M 16/00* (2006.01)
*A61M 16/20* (2006.01)

(52) U.S. Cl.
CPC ...... *A61M 16/107* (2014.02); *A61M 16/0069* (2014.02); *A61M 16/105* (2013.01);
(Continued)

(58) Field of Classification Search
CPC ................ A61M 16/105–107; A61M 16/0069
See application file for complete search history.

(56) References Cited

U.S. PATENT DOCUMENTS 3,690,045 A    9/1972   Delbag
5,183,488 A    2/1993   Deering
(Continued)

FOREIGN PATENT DOCUMENTS

CN    203978677 U    12/2014
CN    204073715 U    1/2015
(Continued)

*Primary Examiner* — Joseph D. Boecker
*Assistant Examiner* — Thomas W Greig

(57) ABSTRACT

An airway pressure support system (2) includes a housing (4) having an air inlet opening (54), and a filter assembly (50) coupled to a plurality of receiving portions of the housing. The filter assembly is in fluid communication with the air inlet opening. The filter assembly includes a housing portion (62), a first filter media portion (64) attached to the housing portion, and first and second spring members (84, 86) attached to the housing portion, wherein the first and second spring members each have a floating portion and engage the plurality of receiving portions and cause a sealing force to be exerted against the filter assembly.

20 Claims, 12 Drawing Sheets

Related U.S. Application Data

(60) Provisional application No. 62/140,488, filed on Mar. 31, 2015.

(52) U.S. Cl.
CPC ... *A61M 16/204* (2014.02); *A61M 2016/0039* (2013.01); *A61M 2205/50* (2013.01); *A61M 2205/502* (2013.01); *A61M 2205/52* (2013.01)

(56) References Cited

U.S. PATENT DOCUMENTS

| | | | |
|---|---|---|---|
| 5,217,606 A | 6/1993 | Ramponi et al. | |
| 5,295,602 A | 3/1994 | Swanson | |
| 5,379,506 A * | 1/1995 | Park | B01D 46/0005 29/451 |
| 5,413,096 A | 5/1995 | Hart | |
| 6,849,107 B1 | 2/2005 | Huffman | |
| 7,634,998 B1 * | 12/2009 | Fenley | A61M 16/0816 128/200.14 |
| 10,967,145 B2 * | 4/2021 | DiMatteo | A61M 16/0069 |
| 2006/0201120 A1 * | 9/2006 | Wu | B01D 46/009 55/495 |
| 2008/0196722 A1 * | 8/2008 | Kramer | A61M 16/024 128/204.22 |
| 2009/0249957 A1 | 10/2009 | Ackey | |
| 2011/0167776 A1 * | 7/2011 | Gorg | F02M 35/02408 55/493 |
| 2013/0197664 A1 * | 8/2013 | Ballard | B01D 39/04 623/23.72 |
| 2015/0013293 A1 | 1/2015 | Wagner | |

FOREIGN PATENT DOCUMENTS

| | | | | |
|---|---|---|---|---|
| DE | 102010047565 A1 | 4/2012 | | |
| EP | 1537903 A1 * | 6/2005 | ......... | B01D 46/0005 |
| EP | 1537903 A1 | 6/2005 | | |
| EP | 2803387 A2 | 11/2014 | | |
| JP | 2001120937 A | 5/2001 | | |
| JP | 2006132892 A | 5/2006 | | |

\* cited by examiner

Flow

FILTER ASSEMBLY AND AIRWAY PRESSURE SUPPORT SYSTEM EMPLOYING SAME

CROSS-REFERENCE TO PRIOR APPLICATIONS

This application is the divisional application of U.S. Ser. No. 15/561,795, filed 26 Sep. 2017, which is a U.S. National Phase application under 35 U.S.C. § 371 of International Application Serial No. PCT/EP2016/056766, filed on 29 Mar. 2016, which claims the benefit of U.S. Application Ser. No. 62/140,488, filed on 31 Mar. 2015 and European Application No. 15166118.8, filed on 1 May 2015. These applications are hereby incorporated by reference herein.

FIELD OF THE INVENTION

The present invention relates to airway pressure support systems, and, more particularly, to a filter assembly for use with an airway pressure support system, and an airway pressure support system employing such a filter assembly.

BACKGROUND OF THE INVENTION

EP1537903 discloses a respirator comprises a housing enclosing a fan or air pump, protected by a coarse filter, and a fine (breathing air quality) filter. The support frame of the fine filter forms an integral component of the locating frame for the coarse filter, so that its absence prevents installation of the coarse screen, and renders the housing visibly incomplete.

DE102010047565 discloses a respiration device has an air intake aperture for intake of ambient air. A hygiene automatic backwashable cartridge (ABC) filter is positioned in the region of air intake aperture for filtering the virus and bacteria in air flow to 99%.

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically, the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

It is well known to treat sleep disordered breathing by applying a positive airway pressure (PAP) to the patient's airway using an airway pressure support system that typically includes a mask, a pressure generating device, and a conduit to deliver positive pressure breathing gas from the pressure generating device to the patient through the mask. This positive pressure effectively "splints" the airway, thereby maintaining an open passage to the lungs. In one type of PAP therapy, known as continuous positive airway pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Air filters, specifically air inlet filters, are an important part of airway pressure support systems. Not only do they protect the inner workings of the device by preventing foreign matter from entering the unit, but they also protect the patient from airborne contaminants. In the current airway pressure support system market, air filters are typically die cut pieces of filter media that sit at the air inlet of the device.

There are two types of air filters that are commonly used in airway pressure support systems. The first type of filter, referred to as a coarse particle filter, is structured to trap and filter relatively large pieces of gross particulate matter from the air before it enters the airway pressure support system. The second type of filter, referred to as a fine particle filter, is designed to be employed in combination with a coarse particle filter and is structured to trap and filter smaller pieces of particulate matter and airborne contaminants that would not otherwise be filtered by the coarse particle filter. Use of a fine particle filter in an airway pressure support system is typically optional. Thus, in practice, an airway pressure support system may be used with a coarse particle filter alone or with a combination of a coarse particle filter and a fine particle filter. When used in combination, the coarse particle filter and fine particle filter are placed in series with one another. To ensure adequate filtration, these filters should create an airtight seal between each other and with the device itself. However, in current practice, the coarse particle filter and fine particle filter media are simply placed on top of each other without any mechanism for applying a force to provide a secure seal.

In addition, coarse particle filters and fine particle filters are designed to be replaced and reimbursed by most insurance companies at different time intervals. Most commonly, the coarse particle filter is replaced every six months and the fine particle filter is replaced every thirty days.

SUMMARY OF THE INVENTION

There is thus a need for a filter assembly for devices such as airway pressure support devices that is able to apply a sealing force in order to ensure a secure seal as described above and that is able to hold both a coarse filter media and a fine filter media in a manner in which the fine filter media may be readily and easily replaced numerous times over the life of the coarse filter media. The invention is defined by the independent claims. The dependent claims define advantageous embodiments.

In one embodiment, an airway pressure support system, is provided that includes a housing having an air inlet opening, a gas flow generator provided within the housing, the gas flow generator being in fluid communication with the air inlet opening and being adapted to produce a flow of gas for delivery to a patient circuit operatively coupled to the gas flow generator, and a filter assembly coupled to a plurality of receiving portions of the housing. The filter assembly is in fluid communication with the air inlet opening. The filter assembly includes a housing portion, a first filter media portion attached to the housing portion, and a plurality of spring members attached to the housing portion, wherein the plurality of spring members engage the plurality of receiving portions and cause a sealing force to be exerted against the filter assembly.

In another embodiment, a filter apparatus structured to be coupled to a housing of a device that employs a gas provided to the device through the filter apparatus is provided. The filter apparatus includes a housing portion having a first opening and a second opening in fluid communication with the first opening, a first filter media portion attached to the housing portion such that the first filter media portion covers the second opening and such that the housing portion and the first filter media portion define a chamber; and a plurality of spring members attached to the housing portion, wherein the housing portion and the plurality of spring members are a unitary component, and wherein the plurality of spring members are structured to engage a plurality of receiving portions of the housing of the device to cause a sealing force to be exerted against the filter apparatus.

In yet another embodiment, a filter member is provided that includes a frame portion including an inner frame portion forming an opening, the inner frame portion including a plurality of inner walls positioned around the opening, and an outer frame portion including a plurality of outer walls. A first one of the inner walls and a first one of the outer walls forms a first groove and a second one of the inner walls and a second one of the outer walls forms a second groove, wherein the first groove is structured to receive a first portion of a housing portion of a second filter member and the second groove is structured to receive a second portion of the housing portion of the second filter member. The inner frame portion is structured to be received within the housing portion of the second filter member to releasably secure the filter member to the second filter member. The filter member also includes a filter media portion attached to the frame portion and covering the opening.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
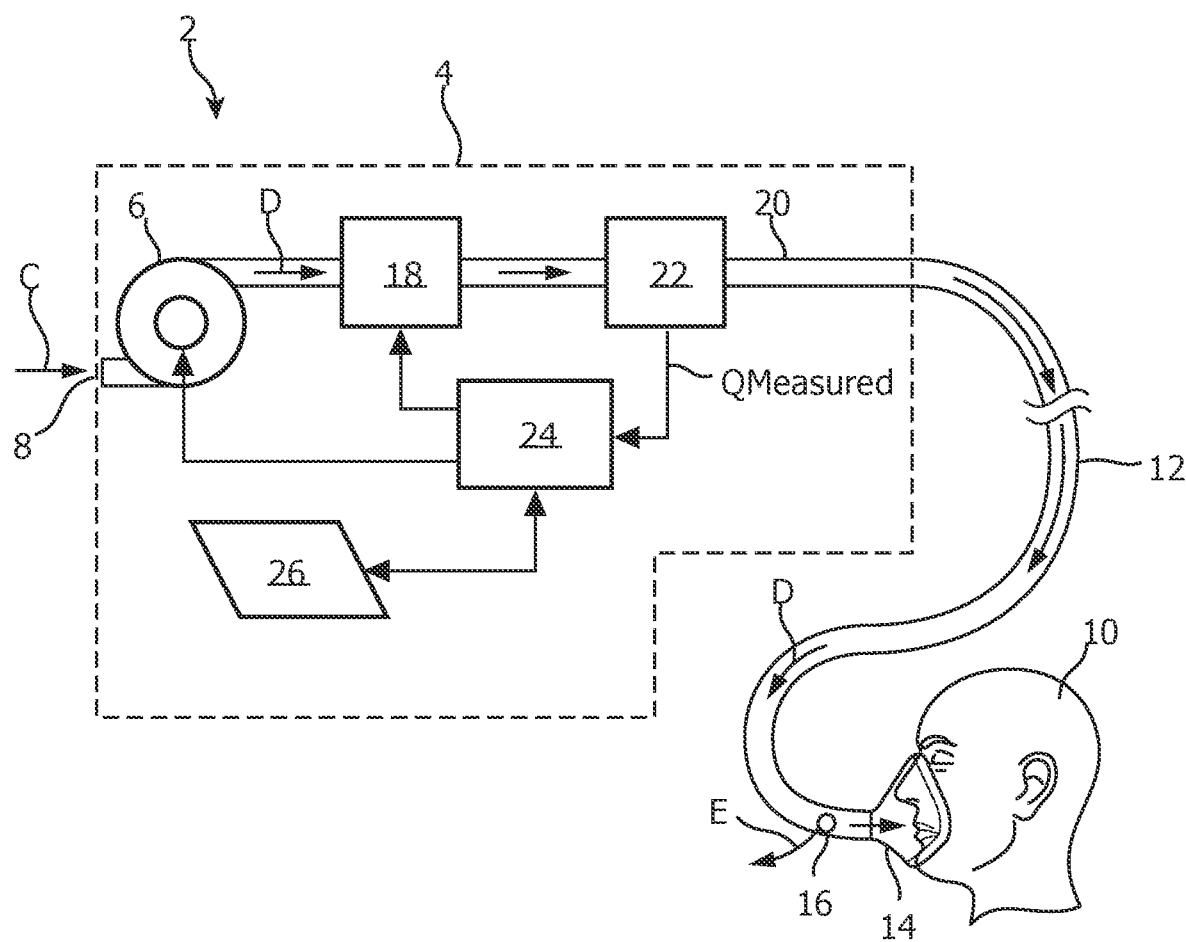
FIG. 1 is a schematic diagram of an airway pressure support system according to one particular, non-limiting embodiment in which the present invention in its various embodiments may be implemented.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of an airway pressure support system 2 according to one particular, non-limiting exemplary embodiment in which the present invention may be implemented. Referring to FIG. 1, airway pressure support system 2 includes a housing 4 which houses a gas flow generator 6, such as a blower used in a conventional CPAP or bi-level pressure support device. Gas flow generator 6 receives breathing gas, generally indicated by arrow C, from the ambient atmosphere through a filtered air inlet 8 (described in greater detail herein) provided as part of housing 4, and generates a flow of breathing gas therefrom for delivery to an airway of a patient 10 at relatively higher and lower pressures, i.e., generally equal to or above ambient atmospheric pressure. In the exemplary embodiment, gas flow generator 6 is capable of providing a flow of breathing gas ranging in pressure from 3-30 cmH$_2$O. The pressurized flow of breathing gas from gas flow generator 6, generally indicated by arrow D, is delivered via a delivery conduit 12 to a breathing mask or patient interface 14 of any known construction, which is typically worn by or otherwise attached to patient 10 to communicate the flow of breathing gas to the airway of patient 10. Delivery conduit 12 and patient interface device 14 are typically collectively referred to as a patient circuit.

Pressure support system 2 shown in FIG. 1 is what is known as a single-limb system, meaning that the patient circuit includes only delivery conduit 12 connecting patient 10 to pressure support system 2. As such, an exhaust vent 16 is provided in delivery conduit 12 for venting exhaled gases from the system as indicated by arrow E. It should be noted that exhaust vent 16 can be provided at other locations in addition to or instead of in delivery conduit 12, such as in patient interface device 14. It should also be understood that exhaust vent 16 can have a wide variety of configurations depending on the desired manner in which gas is to be vented from pressure support system 2.

The present invention also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 14 is a nasal/oral mask. It is to be understood, however, that patient interface 14 can include a nasal mask, nasal pillows, a tracheal tube, an endotracheal tube, or any other device that provides a suitable gas flow communicating function. Also, for purposes of the present invention, the phrase "patient interface" can include delivery conduit 12 and any other structures that couple the source of pressurized breathing gas to patient 10.

In the illustrated embodiment, pressure support system 2 includes a pressure controller in the form of a valve 18 provided in internal delivery conduit 20 provided in housing 4 of pressure support system 2. Valve 18 controls the pressure of the flow of breathing gas from gas flow generator 6 that is delivered to patient 10. For present purposes, gas flow generator 6 and valve 18 are collectively referred to as a pressure generating system because they act in concert to control the pressure and/or flow of gas delivered to patient 10. However, it should be apparent that other techniques for controlling the pressure of the gas delivered to patient 10, such as varying the blower speed of gas flow generator 6, either alone or in combination with a pressure control valve, are contemplated by the present invention. Thus, valve 18 is optional depending on the technique used to control the pressure of the flow of breathing gas delivered to patient 10. If valve 18 is eliminated, the pressure generating system corresponds to gas flow generator 6 alone, and the pressure of gas in the patient circuit is controlled, for example, by controlling the motor speed of gas flow generator 6.

Pressure support system 2 further includes a flow sensor 22 that measures the flow of the breathing gas within delivery conduit 20 and delivery conduit 12. In the particular embodiment shown in FIG. 1, flow sensor 22 is interposed in line with delivery conduits 20 and 12, most preferably downstream of valve 18. Flow sensor 22 generates a flow signal, $Q_{MEASURED}$, which is provided to a controller 24 and is used by controller 24 to determine the flow of gas at patient 10 ($Q_{PATIENT}$).

Techniques for calculating $Q_{PATIENT}$ based on $Q_{MEASURED}$ are well known, and take into consideration the pressure drop of the patient circuit, known leaks from the system, i.e., the intentional exhausting of gas from the circuit as indicated by arrow E in FIG. 1, and unknown leaks from the system, such as leaks at the mask/patient interface. The present invention contemplates using any known or hereafter developed technique for calculating leak flow $Q_{LEAK}$, and using this determination in calculating $Q_{PATIENT}$ based on $Q_{MEASURED}$. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 10 are contemplated by the present invention, such as, without limitation, measuring the flow directly at patient 10 or at other locations along delivery conduit 12, measuring patient flow based on the operation of gas flow generator 6, and measuring patient flow using a flow sensor upstream of valve 18.

Controller 24 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of airway pressure support system 2, including automatically controlling humidity as described in greater detail herein.

An input/output device 26 is provided for setting various parameters used by airway pressure support system 2, as well as for displaying and outputting information and data to a user, such as a clinician or caregiver.

In the illustrated, non-limiting exemplary embodiment of the present invention, airway pressure support system 2 essentially functions as a CPAP pressure support system, and, therefore, includes all of the capabilities necessary in such systems in order to provide appropriate CPAP pressure levels to patient 10. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 2:
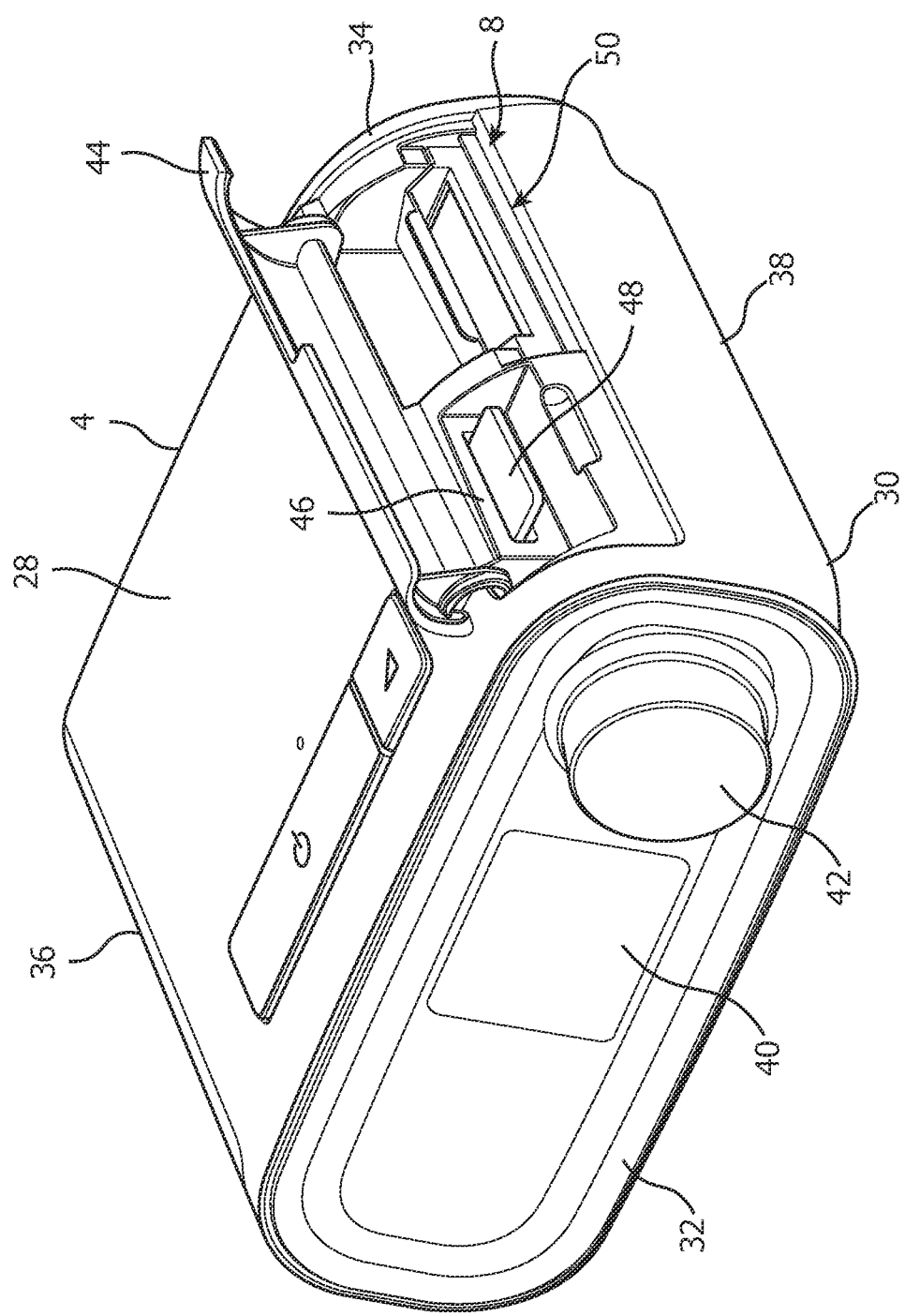
FIGS. 2, 3, 4 and 11 are isometric views of a housing of the airway pressure support system of FIG. 1 according to one particular, non-limiting exemplary embodiment.
Figure 3:
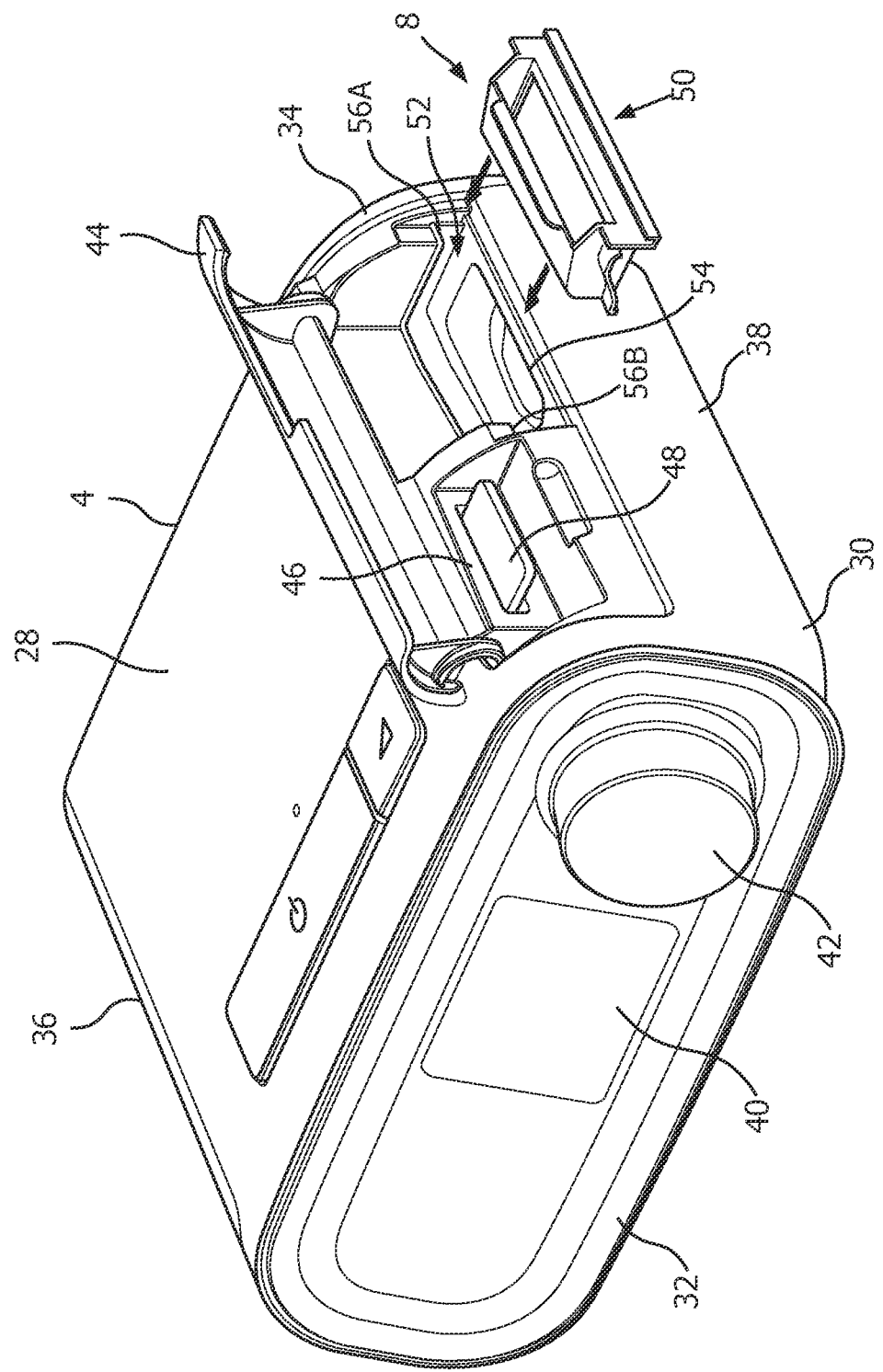
Figure 4:
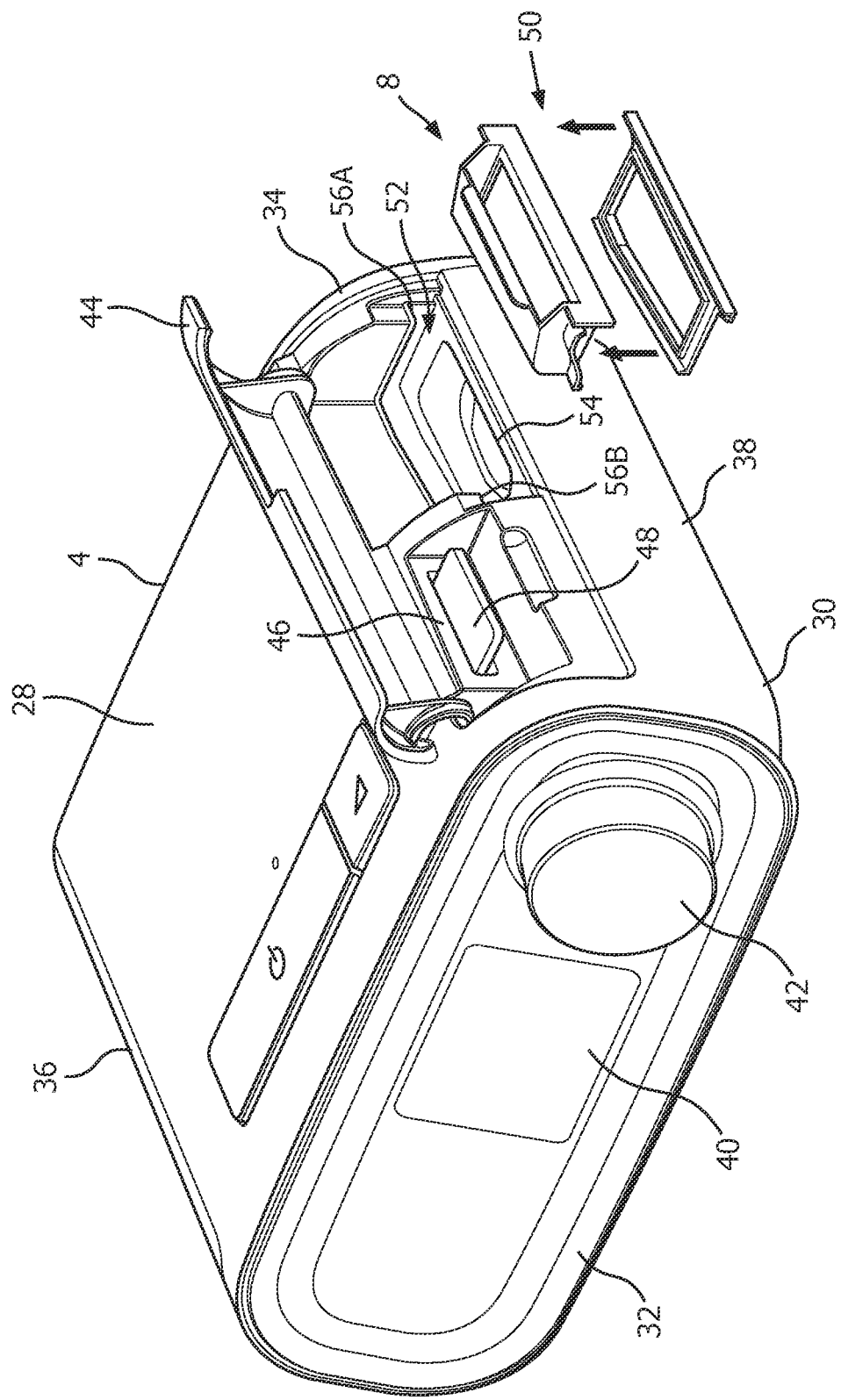
Figure 5:
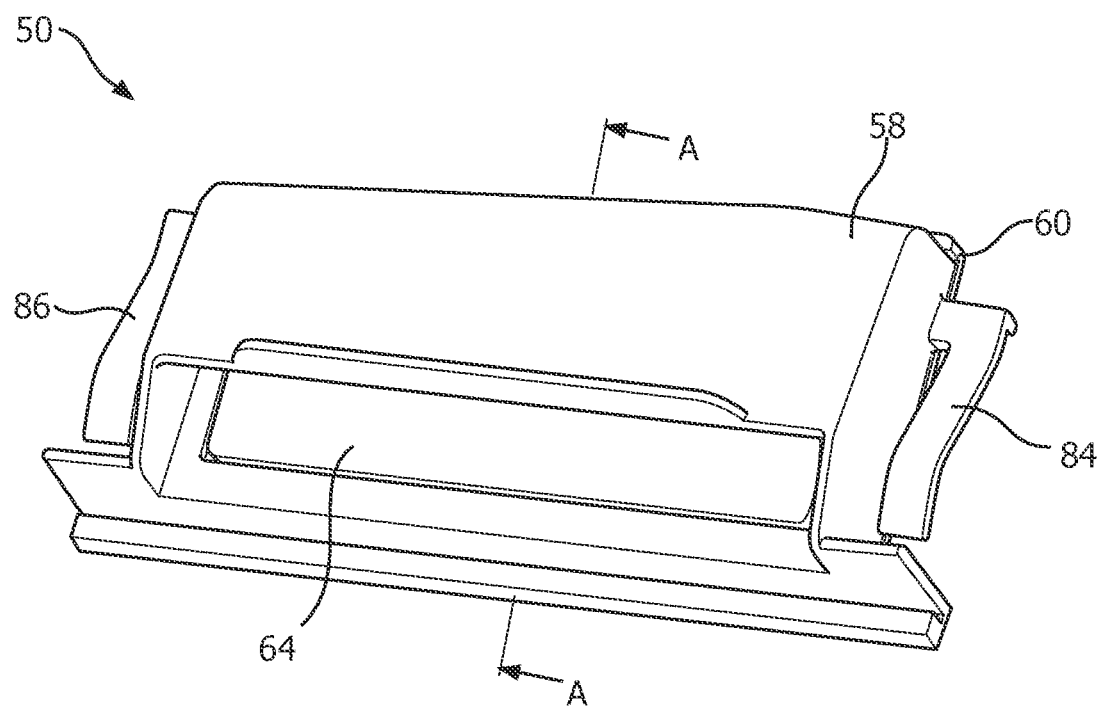
FIGS. 5, 6, 7 and 8 are isometric, side elevational, front elevational, and bottom plan views, respectively, of a filter assembly of the airway pressure support system of FIG. 1 according to one particular, non-limiting exemplary embodiment.
Figure 6:
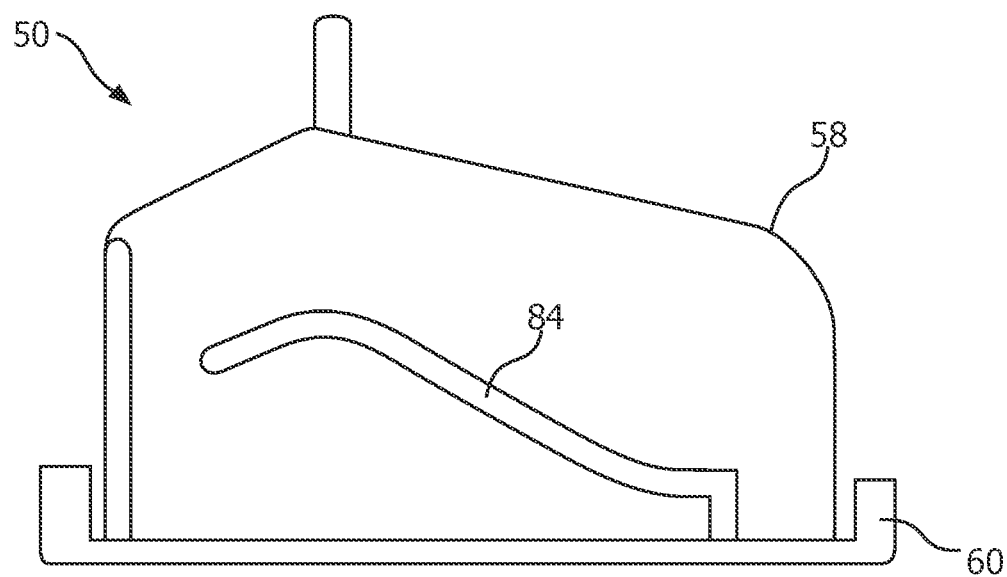
Figure 7:
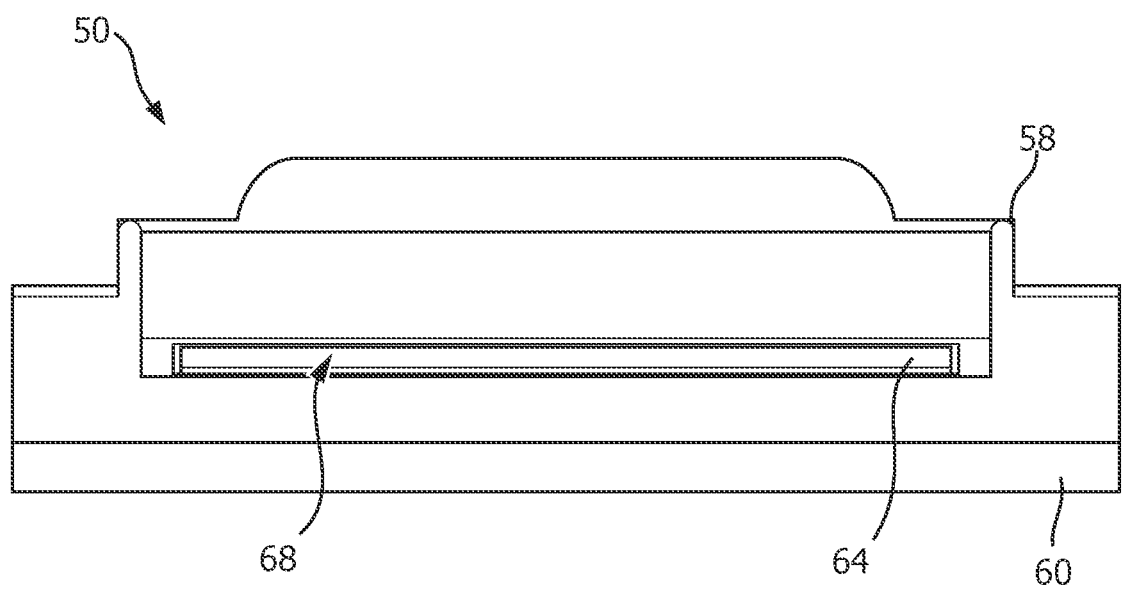
Figure 8:
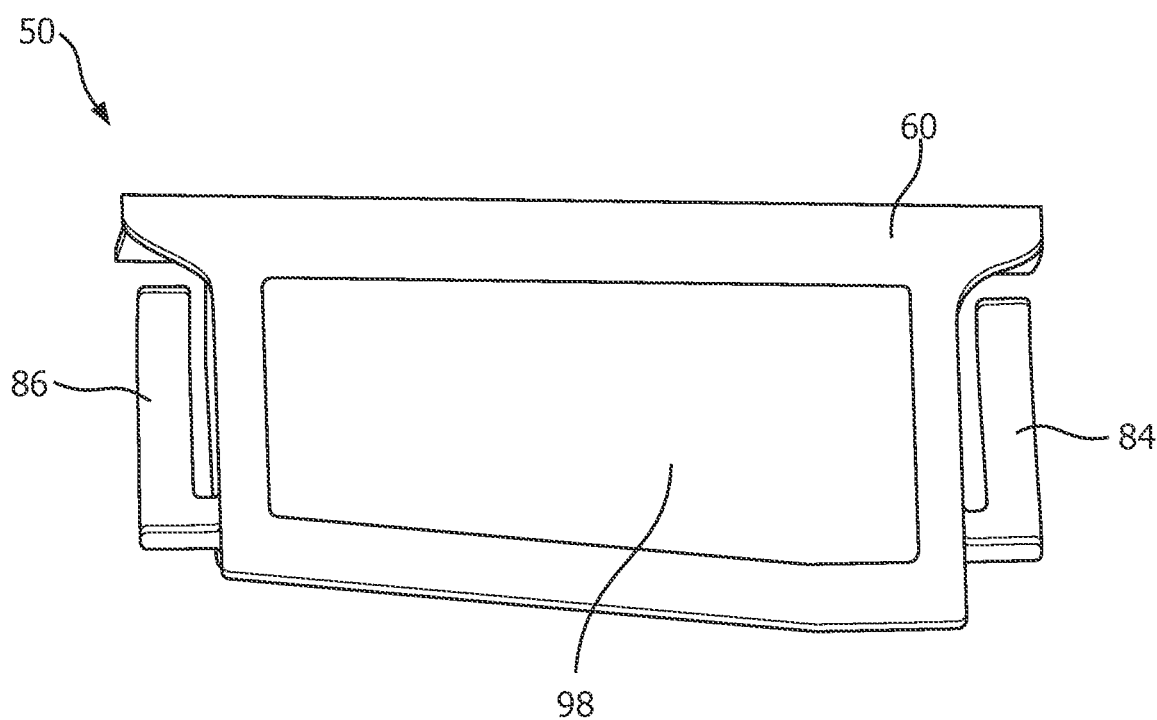

FIGS. 2, 3 and 4 are isometric views of housing 4 of airway pressure support system 2 according to one particular, non-limiting exemplary embodiment. FIG. 2 shows housing 4 in a fully assembled condition and FIGS. 3 and 4 show housing 4 in partially disassembled conditions described below. Housing 4 is constructed from multiple components and, when assembled, includes a top wall 28, a bottom wall 30, a front wall 32, a rear wall 34, a first side wall 36 and a second side wall 38. As seen in FIGS. 2-4, front wall 32 includes input/output device 26 in the form of a display screen 40 and an input dial 42. In addition, as also seen in FIGS. 2-4, second side wall 38 includes an access door 44 which covers and provides selective access to a data port 46 which receives a storage device 48 (e.g., an SD card) for storing therapy related data generated during use of airway pressure support system 2. Access door 44 also provides selective access to filtered air inlet 8. In the exemplary embodiment, filtered air inlet 8 comprises a port structure 52 (shown in FIGS. 3 and 4) and a two piece filter assembly 50 that is structured to be selectively coupled to and received within the port structure 52.

FIG. 2 shows filter assembly 50 in an assembled condition and received within port structure 52, FIG. 3 shows filter assembly 50 in an assembled condition but removed from port structure 52, and FIG. 4 shows filter assembly 50 is a disassembled condition and removed from port structure 52. As seen in FIGS. 3 and 4, port structure 52 includes an opening 54 which provides fluid access to the input of blower 6 to enable air, filtered by filter assembly 50, to be drawn into gas flow generator 6. Port structure 52 also includes a first slot member 56A and a second slot member 56B positioned adjacent to opposite sides of opening 54. First slot member 56A and second slot member 56B each generally have a "square C" shape including first and second side wall portions on opposite sides of a central wall portion. The significance of this feature is described elsewhere herein.

Figure 9:
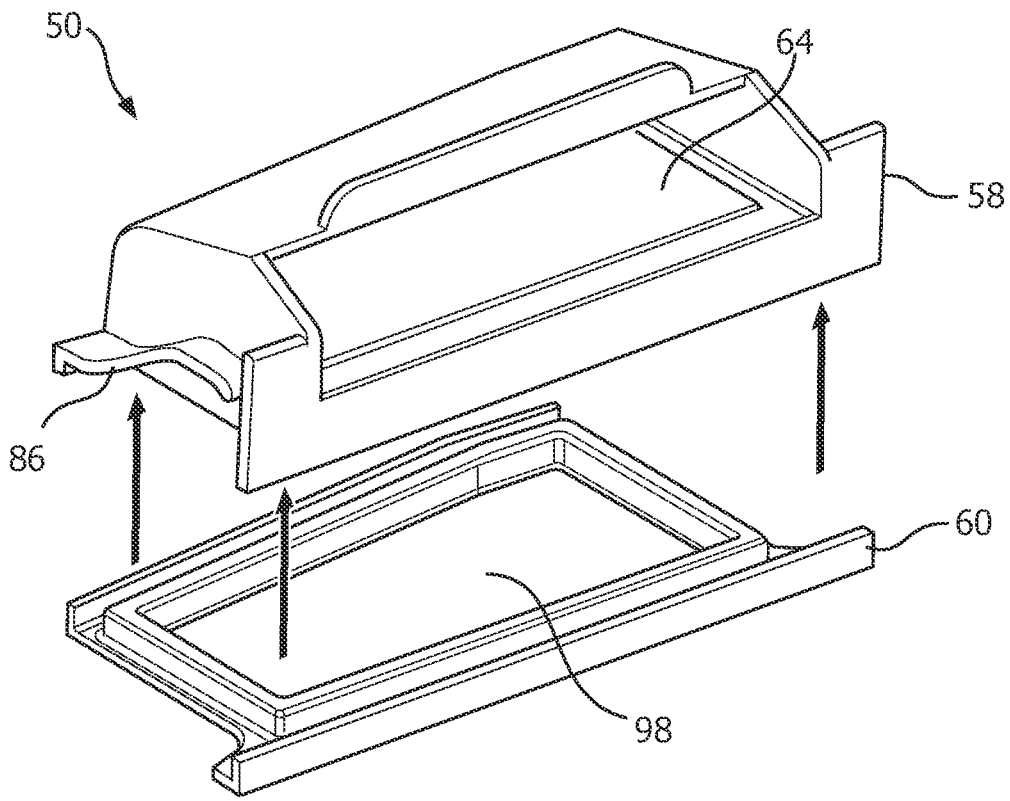
FIG. 9 is an exploded view of the filter assembly of FIGS. 5-8.
Figure 10:
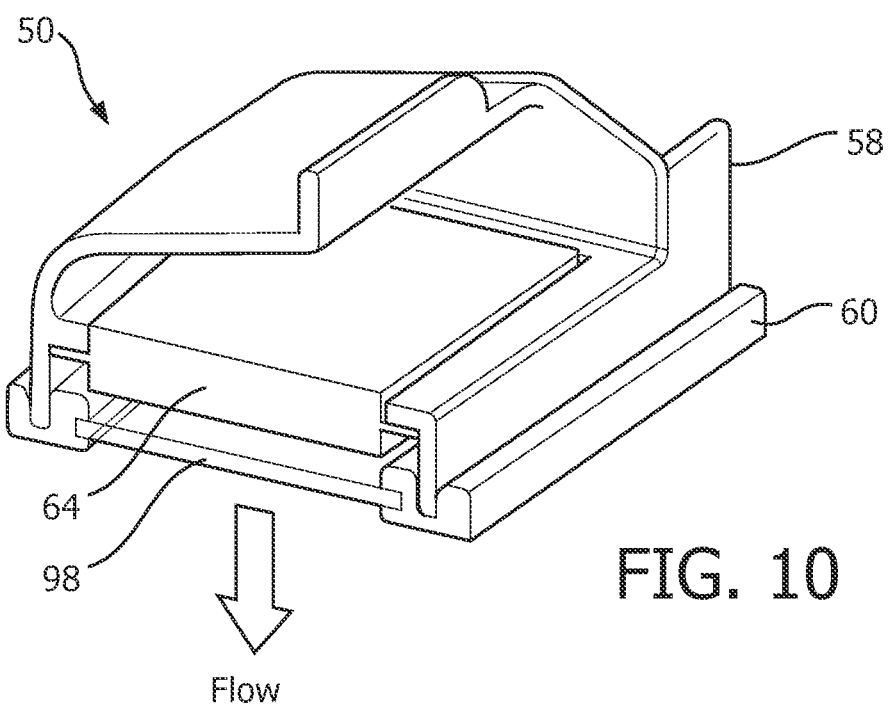
FIG. 10 is a cross-sectional view of the filter assembly of FIGS. 5-8 taken along lines A-A FIG. 5.

FIGS. 5, 6, 7 and 8 are isometric, side elevational, front elevational, and bottom plan views, respectively, of filter assembly 50 in an assembled condition. FIG. 9 is an exploded view of filter assembly 50, and FIG. 10 is a cross-sectional view of filter assembly 50 taken along lines A-A in FIG. 5. As seen in FIGS. 5-10, filter assembly 50 includes a coarse particle filter member 58 that is structured to be selectively and releasably attached to a fine particle filter member 60 in a manner wherein a generally airtight seal is provided between the two members. As described in detail elsewhere herein, in one aspect, filter assembly 50 is structured to be coupled to housing 4 at port structure 52 to provide both coarse particle and fine particle filtering in a manner in which a sealing force is automatically applied to coarse particle filter 58 and fine particle filter 60. Such a force ensures that a secure seal is provided between those two components and between filter assembly 50 and housing 4. In addition, as also described herein, coarse particle filter member 58 is structured to be able to hold multiple similarly structured fine particle filter members 60 over the life of coarse particle filter member 50 due to the releasable connection between the two members. Furthermore, as described in detail herein, in another aspect shown in FIG. 11, coarse particle filter member 58 is also structured to be coupled to housing port 4 at port structure 52 without fine particle filter member 60 in a manner wherein a sealing force is automatically applied to coarse particle filter member 58 to ensure that a secure seal is provided directly between coarse particle filter member 58 and housing 4.

FIGS. 12, 13, 14 and 15 are top plan, bottom plan, side elevational and front elevational views, respectively, of coarse particle filter member 58 according to the exemplary embodiment. Coarse particle filter member 58 includes a housing portion 62 and a coarse particle filter media portion 64 attached to housing portion 62 within a first opening provided in housing portion 62. In the non-limiting, exemplary embodiment, housing portion 62 is made of a resilient material such as, without limitation, an injection molded thermoplastic or silicone. Coarse particle filter media portion 64 is, in the non-limiting exemplary embodiment, a piece of woven or non-woven fabric (e.g., polyester) filter material that is attached to housing portion 62 by any suitable means, such as, without limitation, ultrasonic welding. In the exemplary embodiment, coarse particle filter media portion 64 is a single layer material that has a filtration capacity and pressure drop that are each lower than the filtration capacity and pressure drop of fine particle filter 60.

Housing portion 62 includes a main housing portion 66 and an opening 68 providing access to a chamber defined by main housing portion 66. As will be appreciated, opening 68 is structured to permit the flow of gas through coarse particle filter member 58 and in particular through coarse particle filter media portion 64. In addition, main housing portion 66 includes a bottom perimeter portion 70 including edge portions 72, 74, 76 and 78 which define a second opening spaced from the first opening described above. Also, main housing portion 66 includes sidewalls 80 and 82 provided on opposite lateral sides of main housing portion 66. Finally, housing portion 62 of coarse particle filter member 58 includes a first spring member 84 attached to side wall 80 and a second spring member 86 attached to side wall 82.

Figure 14:
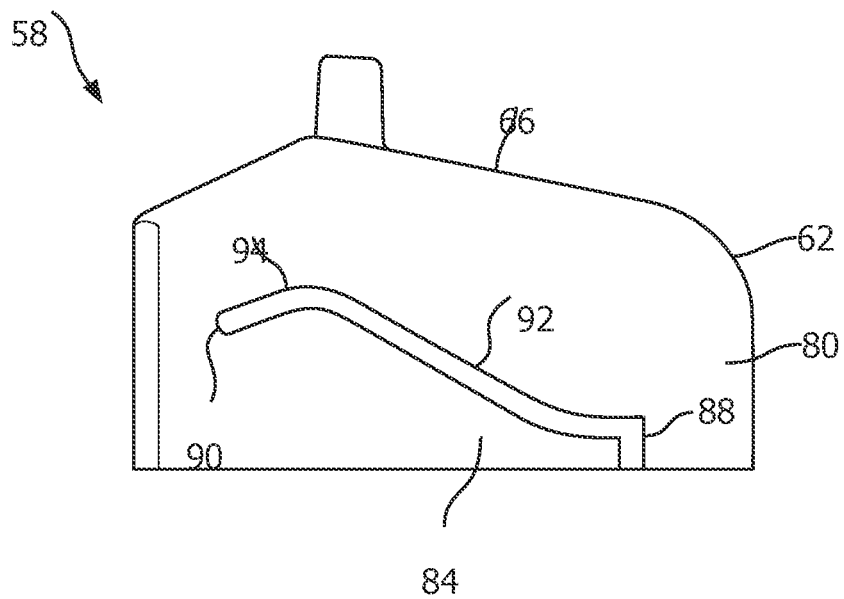
Figure 15:
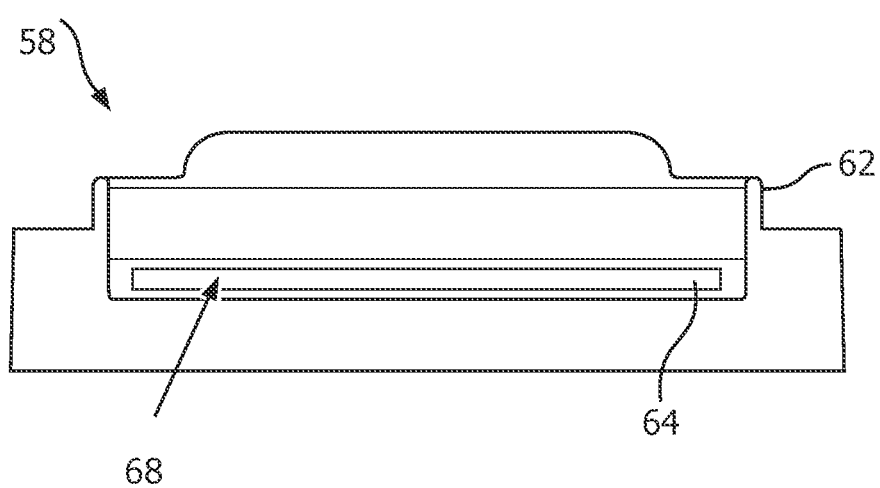

In the illustrated, exemplary embodiment, first spring member 84 and second spring member 86 are each elongated arm members made out of the same material as main housing portion 66 (e.g., molded with main housing portion 66) and each include a proximal end 88 attached to the associated side wall 80, 82 and a free moving (i.e., floating) distal end 90. In addition, as seen in FIG. 14, the arm member of first spring member 84 and second spring member 86 includes a ramp portion 92 directly connected to the proximal end 88 and an arced portion 94 at the distal end 90. The significance of these features is described elsewhere herein.

Furthermore, it will be appreciated that the particular embodiments of first spring member 84 and second spring member 86 described above are just one exemplary embodiment, and that first spring member 84 and second spring member 86 may take on different structures within the scope of the present invention. For example, and without limitation, first spring member 84 and second spring member 86 may be separate spring components (e.g., metal coil springs) that are attached to sidewalls 80 and 82.

Figure 16:
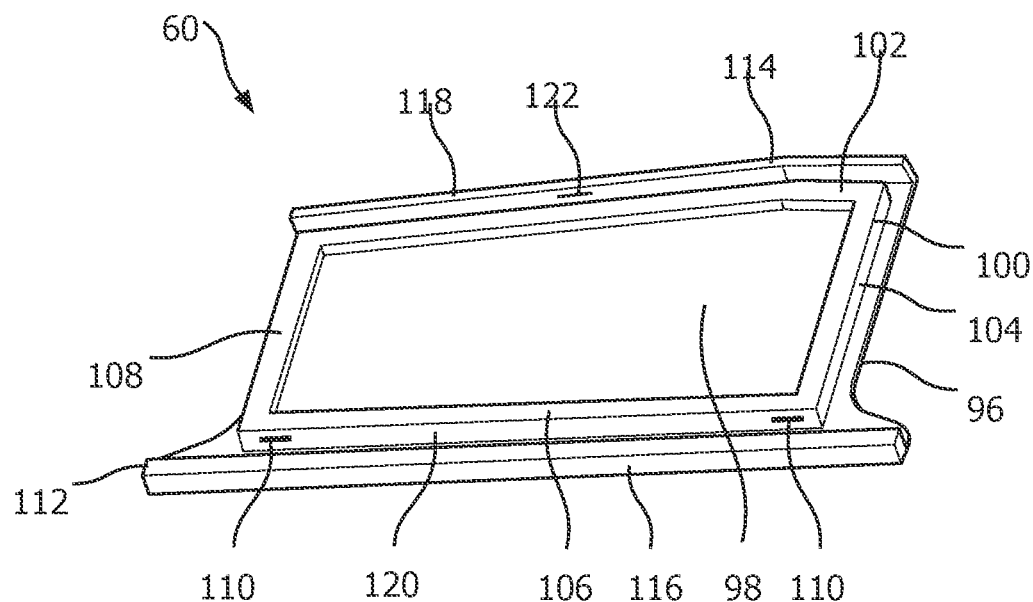
FIGS. 16, 17 and 18 are isometric, top plan, and bottom plan views, respectively, of fine particle filter member of the filter assembly of FIGS. 5-8 according to the exemplary embodiment.
Figure 17:
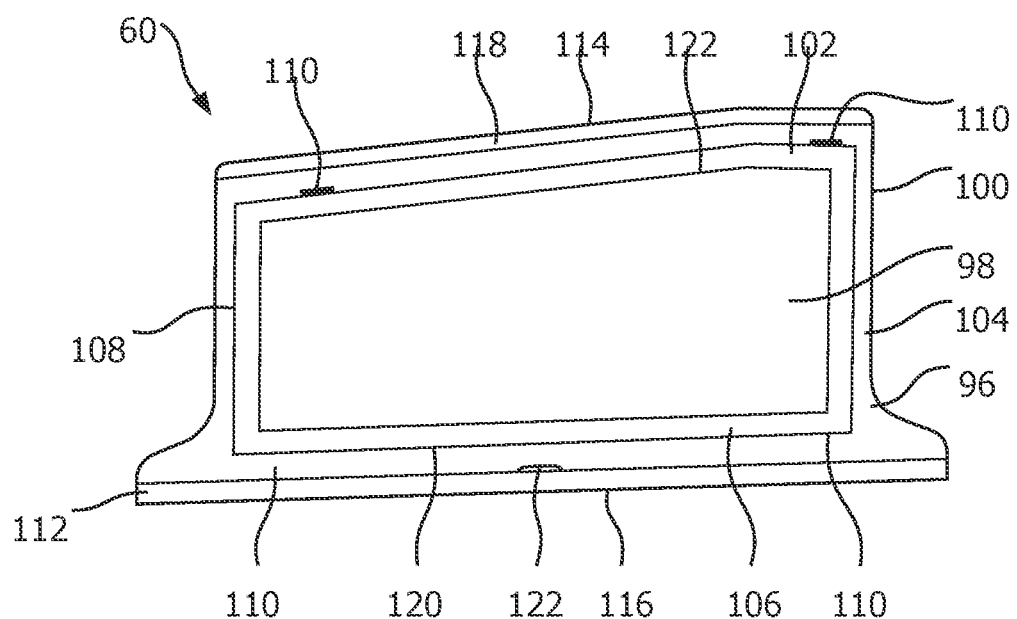
Figure 18:
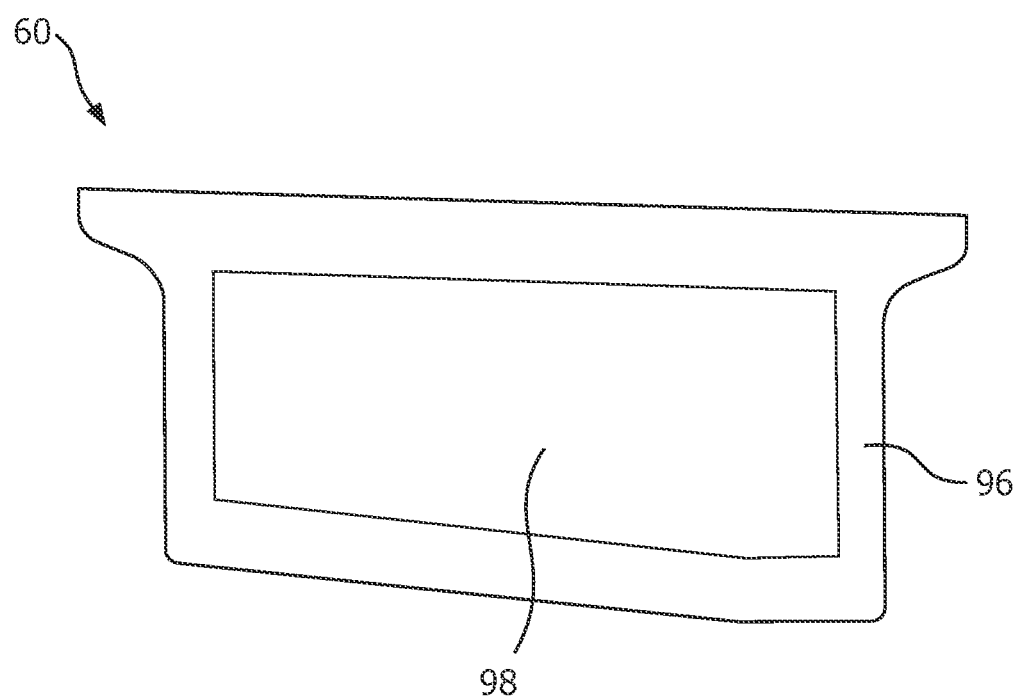

FIGS. 16, 17 and 18 are isometric, top plan, and bottom plan views, respectively, of fine particle filter member 60 according to the exemplary embodiment. Fine particle filter member 60 includes a frame portion 96 and a fine particle filter media portion 98 attached to frame portion 96. In the non-limiting, exemplary embodiment, frame portion 96 is made of an elastomeric material that is softer than the material of main housing portion 66 such as, without limitation, an injection molded thermoplastic elastomer. In one exemplary embodiment, frame portion 96 is made of a material having a durometer of about 40-90 Shore A (in one particular embodiment, frame portion 96 is made of a material having a durometer of about 70-80 Shore A). In contrast, main housing portion 66 is made of a much harder material, such as a thermoplastic (e.g., polycarbonate), which may have a durometer rating of 75-90 Rockwell M. Fine particle filter media portion 98 is, in the non-limiting exemplary embodiment, a piece of woven or non-woven fabric (e.g., polyester) filter material that is attached to frame portion 96 by any suitable means, such as, without limitation, an overmolding process. In the exemplary embodiment, fine particle filter media portion 98 is a non-woven synthetic material having multiple layers for greater filtration and may be made of a blended synthetic fiber and spunbond polypropylene.

Frame portion 96 includes an inner frame portion 100 forming an aperture over which fine particle filter media portion 98 is positioned. Inner frame portion 100 includes walls 102, 104, 106, and 108. Walls 102 and 106 include protruding members 110 extending therefrom, the function of which is described elsewhere herein. In addition, frame portion 96 includes an outer frame portion 112 including outer walls 114 and 116. As seen in FIGS. 16 and 17, wall 102 and outer wall 114 form a first groove 118 and wall 106 and outer wall 116 form a second groove 120. In addition, outer wall 114 and outer wall 116 each include a number of protruding members 122. The function of these elements is described below.

Referring to FIG. 9, filter assembly 50 is assembled by inserting edge portions 72 and 76 of coarse particle filter member 58 into grooves 118 and 120 of fine particle filter member 60. When this is done, inner frame portion 100 will be received within the perimeter created by the inside of edge portion 72, 74, 76 and 78 in a manner such that those edge portions will engage inner frame portion 100. Furthermore, protruding members 110 and 122 extend onto grooves 118 and 120 and provide an interference/friction fit to hold coarse particle filter member 58 and fine particle filter member 60 together until separated from one another by a user with some degree of force.

After filter assembly 50 is assembled as just described, it may be inserted into port structure 52. In particular, filter assembly 50 is inserted into port structure 52 rear side (i.e. the side opposite opening 68) first in a manner wherein first spring member 84 is received within the first slot member 56A of port member 52 and second spring member 86 is received within second slot member 56B of port member 52. When this is done (see FIG. 2), the top side wall of each slot member 56A, 56B will engage (e.g., directly contact in the illustrated example) the respective distal end 94 of each spring member 84, 86. As a result of such engagement, a downward force will be exerted against both coarse particle filter member 58 and fine particle filter member 60 that will result in a seal being created between those two members and between fine particle filter member 60 and housing 4.

Figure 11:
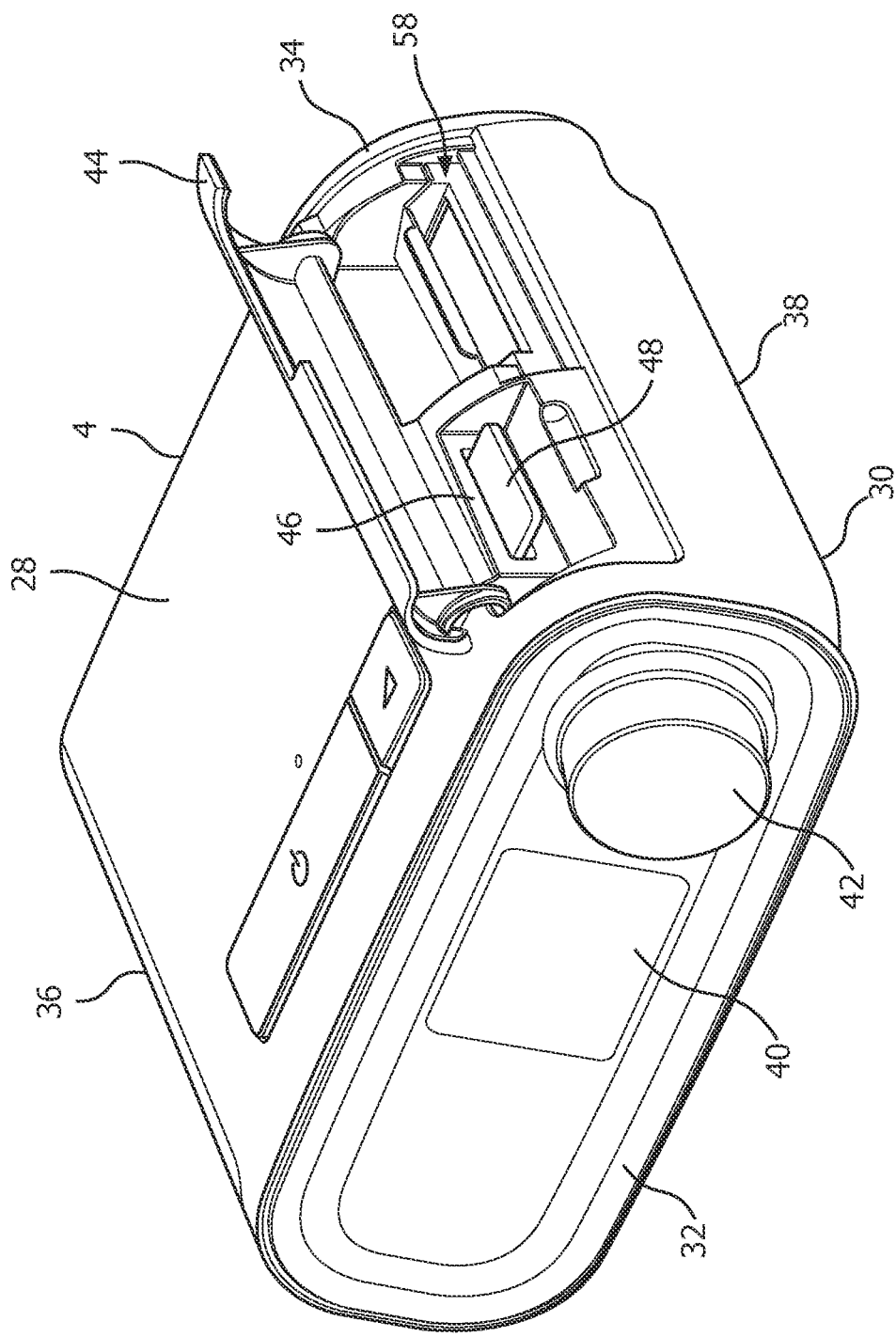
Figure 12:
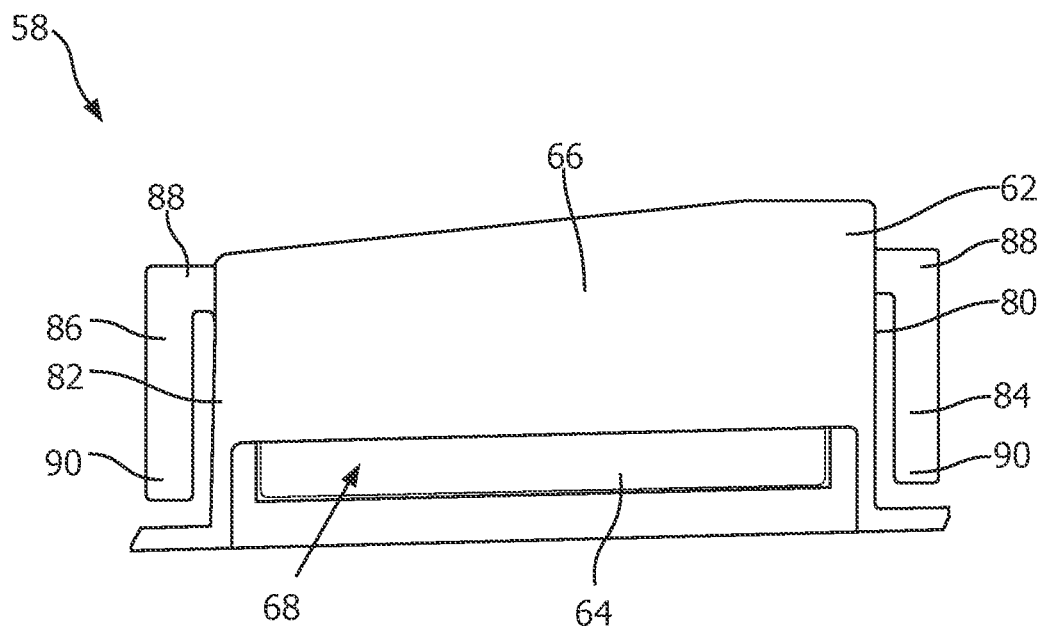
FIGS. 12, 13, 14 and 15 are top plan, bottom plan, side elevational and front elevational views, respectively, of a coarse particle filter member of the filter assembly of FIGS. 5-8 according to the exemplary embodiment.
Figure 13:
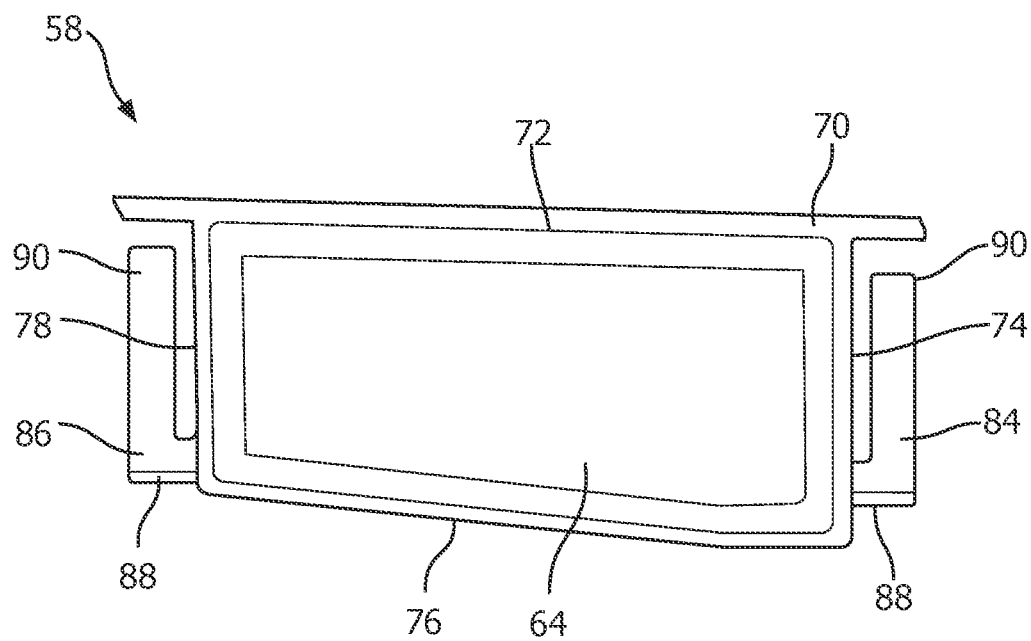

In addition, coarse particle filter member 58 alone (i.e., with fine particle filter member 60 separated therefrom) may also be in inserted into port structure 52 in a like manner when it is desired to provide only coarse filtering capabilities. When this is done, due to the flexible nature of first spring member 84 and second spring member 86, those members will be able to flex and still engage (e.g., directly contact in the illustrated example) the top side wall of each slot member 56A, 56B such that sealing force is exerted and a suitable seal is created between coarse particle filter member 58 and housing 4. This condition is illustrated in FIG. 11.

Thus, the integral spring feature(s) of coarse particle filter member 58 allows it to float and apply a force against the inlet of housing 4. As described above, this float will allow the placement of fine particle filter member 60 in series with coarse particle filter member 58 while still maintaining a force to ensure an airtight seal. In other words, coarse particle filter member 58 will self-adjust depending upon whether it is used by itself or with fine particle filter member 60. As also described above, coarse particle filter member 58 and fine particle filter member 60 are structured and shaped to allow coarse particle filter member 58 to be nested within fine particle filter member 60. This will create good alignment for filtration and allow ease of use for the end user.

Accordingly, as described herein, the disclosed concept provides a filter assembly for devices such as airway pressure support devices that is able to apply appropriate sealing forces the filter assembly and that is also able to hold both a coarse filter media and a fine filter media in a manner that allows the fine filter media to be readily and easily replaced numerous times over the life of the coarse filter media.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

The invention claimed is:

1. A filter apparatus structured to be coupled to a housing of a device that employs a gas provided to the device through the filter apparatus, the filter apparatus comprising:
    a housing portion having a first vertically disposed side wall, a second vertically disposed side wall opposite the first side wall, a front vertically disposed wall provided between the first side wall and the second side wall, a top wall connected to the front wall, the first side wall and the second side wall, and a bottom horizontally disposed portion opposite the top wall and having a first opening formed therein;
    a first filter media portion attached to the bottom portion, wherein the first filter media portion comprises a coarse particle filter member that covers the first opening, the coarse particle filter member having a filtration capacity and pressure drop that are each lower than a filtration capacity and pressure drop of a fine particle filter member, and wherein the first filter media portion, the first side wall, the second side wall, the front wall, the top wall and the bottom portion form an inner chamber having a second opening opposite the front wall and in fluid communication with the first opening, via the first filter media portion; and
    a first spring member provided on an exterior of the first side wall, and a second spring member provided on an exterior of the second side wall, wherein the first and second spring members each have a vertically disposed floating portion configured to engage a respective top wall of a first slot member and a second slot member of a port structure of the housing of the device and provide a downward sealing force to be exerted against the filter apparatus to create a seal between the bottom portion and an air inlet opening of a port structure of the housing of the device, in response to the filter apparatus being inserted into the port structure.

2. A filter assembly including the filter apparatus according to claim 1, wherein the filter assembly comprises a fine particle filter member releasably coupled to the coarse particle filter member, wherein the fine particle filter member includes a second filter media portion positioned in series with the first filter media portion, wherein the second filter media portion is structured to filter a smaller particle size than the first filter media portion.

3. The filter assembly according to claim 2, wherein the first and second spring members are structured to engage the respective top wall of the first slot member and the second slot member and cause the sealing force to be exerted against the coarse particle filter member and the fine particle filter member.

4. The filter assembly according to claim 2, wherein the fine particle filter member comprises a frame portion including an inner frame portion and an outer frame portion disposed outside of the inner frame portion on a common base of the frame portion, the inner frame portion including a plurality of inner walls vertically disposed above the common base and positioned around an opening in the common base, and the outer frame portion including a plurality of outer walls vertically disposed above the common base, wherein a first one of the inner walls and a first one of the outer walls forms a first groove above the common base between the inner frame portion and the outer frame portion and wherein a second one of the inner walls and a second one of the outer walls forms a second groove above the common base between the inner frame portion and the outer frame portion, wherein the first groove is structured to receive a first vertically disposed edge portion of a bottom perimeter portion of the housing portion and the second groove is structured to receive a second vertically disposed edge portion of the bottom perimeter portion of the housing portion, and wherein the inner frame portion is structured to be received within the bottom perimeter portion of the housing portion to releasably secure the fine particle filter member to the coarse particle filter member; and
   wherein the second filter media portion is attached to the inner frame portion and covering the opening.

5. The filter assembly according to claim 4, wherein the first one of the inner walls, the first one of the outer walls, the second one of the inner walls, and the second one of the outer walls each include one or more horizontally disposed protruding members extending outwardly therefrom into a respective one of the first groove and the second groove.

6. The filter assembly according to claim 5, further wherein the one or more horizontally disposed protruding members provide an interference/friction fit to hold a respective one of the first vertically disposed edge portion and the second vertically disposed edge portion of the bottom perimeter portion of the housing portion of the second filter member when received within the first and second grooves.

7. The filter assembly according to claim 4, wherein the plurality of outer walls of the outer frame portion further comprise a single front outer wall and a single rear outer wall, each vertically disposed above the common base, further wherein the first groove comprises a single groove disposed between the front outer wall and a front inner wall of the inner frame portion and the second groove comprises a single groove disposed between a rear inner wall of the inner frame portion and the rear outer wall.

8. A filter member, comprising:
   a frame portion including an inner frame portion and an outer frame portion disposed outside of the inner frame portion on a common base of the frame portion, the inner frame portion including a plurality of inner walls vertically disposed above the common base and positioned around an opening in the common base, and the outer frame portion including a plurality of outer walls vertically disposed above the common base, wherein a number of walls in the plurality of outer walls is less than a number of walls in the plurality of inner walls, leaving at least one portion of the common base without an outer wall of the outer frame portion, the frame portion further including a first groove disposed between a first one of the inner walls of the inner frame portion and a first one of the outer walls of the outer frame portion above the common base and a second groove disposed between a second one of the inner walls of the inner frame portion and a second one of the outer walls of the outer frame portion above the common base, wherein the first groove is structured to receive a first vertically disposed edge portion of a bottom perimeter portion of a housing portion of a second filter member, wherein the second filter member includes a second filter media portion located within the housing portion proximate the bottom perimeter portion and at least one spring member extending from the housing portion proximate the bottom perimeter portion, and wherein the second groove is structured to receive a second vertically disposed edge portion of the bottom perimeter portion of the housing portion of the second filter member, and wherein the inner frame portion is structured to be received within the bottom perimeter portion of the housing portion of the second filter member to releasably secure the filter member to the second filter member, and wherein the at least one portion of the common base without the outer wall of the outer frame portion is adapted to be disposed adjacent the at least one spring member extending from the housing portion proximate the bottom perimeter portion of the second filter member; and
   a first filter media portion attached to the inner frame portion and covering the opening, wherein the first filter media portion comprises filter media adapted to filter a first particle size and wherein the second filter media portion comprises filter media adapted to filter a second particle size, different from the first particle size.

9. The filter member according to claim 8, wherein the first one of the inner walls, the first one of the outer walls, the second one of the inner walls, and the second one of the outer walls each include one or more horizontally disposed protruding members extending outwardly therefrom into a respective one of the first groove and the second groove.

10. The filter member according to claim 9, further wherein the one or more horizontally disposed protruding members provide an interference/friction fit to hold a respective one of the first vertically disposed edge portion and the second vertically disposed edge portion of the bottom perimeter portion of the housing portion of the second filter member when received within the first and second grooves.

11. The filter member according to claim 8, wherein the plurality of outer walls of the outer frame portion further only comprise a single rear outer wall and a single front outer wall, each vertically disposed above the common base, further wherein the first groove comprises a single groove disposed between the rear outer wall and a rear inner wall of the inner frame portion and the second groove comprises a single groove disposed between a front inner wall of the inner frame portion and the front outer wall.

12. An airway pressure support system, comprising:
- a housing having a port structure with an air inlet opening, the air inlet opening being disposed on a horizontal surface of the port structure, the port structure further including a first slot member and a second slot member within a respective first vertical side and second vertical side of the port structure; and
- a filter assembly coupled to the housing via the port structure, the filter assembly being in fluid communication with the air inlet opening, wherein the filter assembly includes a housing portion having a first vertically disposed side wall, a second vertically disposed side wall opposite the first side wall, a front vertically disposed wall provided between the first side wall and the second side wall, a top wall connected to the front wall, the first side wall and the second side wall, and a bottom horizontally disposed portion opposite the top wall and having a first opening formed therein, the filter assembly further including a first filter media portion attached to the bottom portion, wherein the first filter media portion comprises a coarse particle filter member that covers the first opening, the coarse particle filter member having a filtration capacity and pressure drop that are each lower than a filtration capacity and pressure drop of a fine particle filter member, and wherein the first filter media portion, the first side wall, the second side wall, the front wall, the top wall and the bottom portion form an inner chamber having a second opening opposite the front wall and in fluid communication with the first opening, via the first filter media portion, the filter assembly still further including a first spring member provided on an exterior of the first side wall, and a second spring member provided on an exterior of the second side wall, wherein the first and second spring members each have a vertically disposed floating portion configured to engage a respective top wall of the first slot member and the second slot member and provide a downward sealing force to be exerted against the filter assembly to create a seal between the bottom portion of the filter assembly and air inlet opening of the port structure of the housing, in response to the filter assembly being inserted into the port structure.

13. The airway pressure support system according to claim 12, wherein the filter assembly further comprises a fine particle filter member.

14. The airway pressure support system according to claim 13, wherein the housing portion, the first filter media portion, and the first and second spring members are part of the coarse particle filter member, wherein the fine particle filter member includes a second filter media portion positioned in series with the first filter media portion, wherein the second filter media portion is structured to filter a smaller particle size than the first filter media portion, and wherein the first and second spring members engage the respective top wall of the first slot member and the second slot member and cause the sealing force to be exerted against the coarse particle filter member and the fine particle filter member.

15. The airway pressure support system according to claim 13, wherein the fine particle filter member is releasably coupled to the coarse particle filter member.

16. The airway pressure support system according to claim 15, wherein the fine particle filter member includes a frame member, wherein the second filter media portion is attached to the frame member, wherein the housing portion of the filter assembly includes a number of first features structured to be mated with a number of second features of the frame member to enable the fine particle filter member to be releasably coupled to the coarse particle filter member.

17. The airway pressure support system according to claim 16, wherein the number of first features includes a number of edge portions provided on the housing portion of the filter assembly and wherein the number of second features includes a number of grooves provided in the frame member of the fine particle filter.

18. The airway pressure support system according to claim 12, wherein the first spring member comprises a first arm member having a first proximal end connected to the first side wall, wherein the second spring member comprises a second arm member having a second proximal end connected to the second side wall.

19. The airway pressure support system according to claim 18, wherein the floating portion of the first spring member is a floating first distal end of the first arm member, the floating portion of second spring member is a floating second distal end of the second arm member, and wherein the floating first distal end engages a first top wall of the first slot member of the port structure of the housing, and the floating second distal end engages a second top wall of the second slot member of the port structure of the housing.

20. The airway pressure support system according to claim 18, wherein the first arm member includes a first ramp portion directly connected to the first proximal end and a first arced portion at a distal end of the first arm member, and wherein the second arm member includes a second ramp portion directly connected to the second proximal end and a second arced portion at a distal end of the second arm member.

* * * * *